(12) United States Patent
Budiman

(10) Patent No.: US 11,954,273 B2
(45) Date of Patent: Apr. 9, 2024

(54) SYSTEMS, DEVICES AND METHODS FOR MANAGING GLUCOSE LEVELS

(71) Applicant: ABBOTT DIABETES CARE INC., Alameda, CA (US)

(72) Inventor: Erwin S. Budiman, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 18/135,629

(22) Filed: Apr. 17, 2023

(65) Prior Publication Data

US 2023/0251727 A1    Aug. 10, 2023

Related U.S. Application Data

(63) Continuation of application No. 17/343,236, filed on Jun. 9, 2021, which is a continuation of application
(Continued)

(51) Int. Cl.
| | |
|---|---|
| *G06F 3/0362* | (2013.01) |
| *A61B 5/00* | (2006.01) |
| *A61B 5/145* | (2006.01) |
| *A61M 5/172* | (2006.01) |
| *G06F 3/01* | (2006.01) |
| *H01H 3/00* | (2006.01) |

(52) U.S. Cl.
CPC ........ *G06F 3/0362* (2013.01); *A61B 5/14532* (2013.01); *A61M 5/1723* (2013.01); *G06F 3/016* (2013.01); *A61B 5/7455* (2013.01); *A61B 5/746* (2013.01); *A61B 2560/0276* (2013.01); *A61M 2205/18* (2013.01); *A61M 2205/3584* (2013.01); *A61M 2205/505* (2013.01); *A61M 2205/582* (2013.01); *A61M 2230/201* (2013.01); *H01H 2003/008* (2013.01)

(58) Field of Classification Search
CPC .... G06F 3/0362; G06F 3/016; A61M 5/1723; A61M 2205/18; A61M 2205/3584; A61M 2205/505; A61M 2205/582; A61M 2230/201; A61B 5/14532; A61B 5/7455; A61B 5/746; A61B 2560/0276; H01H 2003/008
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |

(Continued)

FOREIGN PATENT DOCUMENTS

| | | |
|---|---|---|
| EP | 0098592 | 1/1984 |
| EP | 0127958 | 12/1984 |

(Continued)

OTHER PUBLICATIONS

PCT/US2011/027794 ISR and Written Opinion.
(Continued)

*Primary Examiner* — Christian Jang
(74) *Attorney, Agent, or Firm* — ONE LLP

(57) ABSTRACT

Systems, devices and methods for the management of glucose levels in the body of patient featuring user interface input mechanisms configured to provide haptic feedback to the user are provided.

19 Claims, 4 Drawing Sheets

Related U.S. Application Data

No. 16/128,100, filed on Sep. 11, 2018, now Pat. No. 11,061,491, which is a continuation of application No. 15/093,010, filed on Apr. 7, 2016, now Pat. No. 10,078,380, which is a continuation of application No. 13/044,521, filed on Mar. 9, 2011, now Pat. No. 9,326,709.

(60) Provisional application No. 61/312,644, filed on Mar. 10, 2010.

(56) References Cited

U.S. PATENT DOCUMENTS

| | | |
|---|---|---|
| 3,949,388 A | 4/1976 | Fuller |
| 3,960,497 A | 6/1976 | Acord et al. |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,199,428 A | 8/1993 | Obel et al. |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,532,686 A | 7/1996 | Urbas et al. |
| 5,543,326 A | 8/1996 | Heller et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Nigel et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,720,295 A | 2/1998 | Greenhut et al. |
| 5,724,030 A | 3/1998 | Urbas et al. |
| 5,733,259 A | 3/1998 | Valcke et al. |
| 5,735,285 A | 4/1998 | Albert et al. |
| 5,741,211 A | 4/1998 | Renirie et al. |
| 5,749,907 A | 5/1998 | Mann |
| 5,771,891 A | 6/1998 | Gozani |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,804,047 A | 9/1998 | Karube et al. |
| 5,820,551 A | 10/1998 | Hill et al. |
| 5,822,715 A | 10/1998 | Worthington et al. |
| 5,891,047 A | 4/1999 | Lander et al. |
| 5,891,049 A | 4/1999 | Cyrus et al. |
| 5,899,855 A | 5/1999 | Brown |

(56) References Cited

U.S. PATENT DOCUMENTS

| | | |
|---|---|---|
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |
| 6,134,461 A | 10/2000 | Say et al. |
| 6,115,628 A | 11/2000 | Stadler et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,296,571 B1 | 10/2001 | McVicar |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |

(56) References Cited

U.S. PATENT DOCUMENTS

| | | |
|---|---|---|
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,978,286 B2 | 12/2005 | Francis et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,225,091 B2 | 5/2007 | Tivig et al. |
| 7,225,535 B2 | 6/2007 | Feldman et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Goode, Jr. et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,347,819 B2 | 5/2008 | Lebel et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,429,255 B2 | 9/2008 | Thompson |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,524,287 B2 | 4/2009 | Bharmi |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |

(56) References Cited

U.S. PATENT DOCUMENTS

| | | |
|---|---|---|
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,736,310 B2 | 6/2010 | Taub et al. |
| 7,741,734 B2 | 6/2010 | Joannopoulos et al. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,889,069 B2 | 2/2011 | Fifolt et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,938,797 B2 | 5/2011 | Estes |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,216,138 B1 | 7/2012 | McGarraugh et al. |
| 8,282,549 B2 | 10/2012 | Brauker et al. |
| 9,326,709 B2 | 5/2016 | Budiman |
| 10,078,380 B2 | 9/2018 | Budiman |
| 2001/0048362 A1 | 12/2001 | Spencer |
| 2002/0019022 A1 | 2/2002 | Dunn et al. |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0128594 A1 | 9/2002 | Das et al. |
| 2002/0130779 A1 | 9/2002 | Ford |
| 2002/0143266 A1 | 10/2002 | Bock |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023461 A1 | 1/2003 | Quintanilla et al. |
| 2003/0032867 A1 | 2/2003 | Crothall et al. |
| 2003/0050546 A1 | 3/2003 | Desai et al. |
| 2003/0100821 A1 | 5/2003 | Heller et al. |
| 2003/0168338 A1 | 9/2003 | Gao et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010207 A1 | 1/2004 | Flaherty et al. |
| 2004/0039298 A1 | 2/2004 | Abreu |
| 2004/0054263 A1 | 3/2004 | Moerman et al. |
| 2004/0064068 A1 | 4/2004 | DeNuzzio et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186365 A1 | 9/2004 | Jin et al. |
| 2004/0197846 A1 | 10/2004 | Hockersmith et al. |
| 2004/0199056 A1 | 10/2004 | Husemann et al. |
| 2004/0204687 A1 | 10/2004 | Mogensen et al. |
| 2004/0208780 A1 | 10/2004 | Faries, Jr. et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0016276 A1 | 1/2005 | Guan et al. |
| 2005/0017864 A1 | 1/2005 | Tsoukalis |
| 2005/0027181 A1 | 2/2005 | Goode et al. |
| 2005/0031689 A1 | 2/2005 | Shults et al. |
| 2005/0043598 A1 | 2/2005 | Goode et al. |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0114068 A1 | 5/2005 | Chey et al. |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0195930 A1 | 9/2005 | Spital et al. |
| 2005/0214892 A1 | 9/2005 | Kovatchev et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277912 A1 | 12/2005 | John |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0017923 A1 | 1/2006 | Ruchti et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0058588 A1 | 3/2006 | Zdeblick |
| 2006/0091006 A1 | 5/2006 | Wang et al. |
| 2006/0166629 A1 | 7/2006 | Reggiardo |
| 2006/0173260 A1 | 8/2006 | Gaoni et al. |
| 2006/0189863 A1 | 8/2006 | Peyser et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0055799 A1 | 3/2007 | Koehler et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0108048 A1 | 5/2007 | Wang et al. |
| 2007/0118405 A1 | 5/2007 | Campbell et al. |
| 2007/0124002 A1 | 5/2007 | Estes et al. |

(56) References Cited

U.S. PATENT DOCUMENTS

| | | |
|---|---|---|
| 2007/0149875 A1 | 6/2007 | Ouyang et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |
| 2007/0299617 A1 | 12/2007 | Willis |
| 2008/0009692 A1 | 1/2008 | Stafford |
| 2008/0018433 A1 | 1/2008 | Pitt-Pladdy |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0064943 A1 | 3/2008 | Talbot et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0083617 A1 | 4/2008 | Simpson et al. |
| 2008/0086273 A1 | 4/2008 | Shults et al. |
| 2008/0097289 A1 | 4/2008 | Steil et al. |
| 2008/0119703 A1 | 5/2008 | Brister et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0183060 A1 | 7/2008 | Steil et al. |
| 2008/0188796 A1 | 8/2008 | Steil et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208113 A1 | 8/2008 | Damiano et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0231970 A1* | 9/2008 | Henderson .............. G02B 7/08 310/317 |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0287761 A1 | 11/2008 | Hayter |
| 2008/0287762 A1 | 11/2008 | Hayter |
| 2008/0287763 A1 | 11/2008 | Hayter |
| 2008/0288180 A1 | 11/2008 | Hayter |
| 2008/0288204 A1 | 11/2008 | Hayter et al. |
| 2008/0300572 A1 | 12/2008 | Rankers et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319279 A1 | 12/2008 | Ramsay et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036760 A1 | 2/2009 | Hayter |
| 2009/0036763 A1 | 2/2009 | Brauker et al. |
| 2009/0043182 A1 | 2/2009 | Brauker et al. |
| 2009/0043525 A1 | 2/2009 | Brauker et al. |
| 2009/0048503 A1 | 2/2009 | Dalal et al. |
| 2009/0054745 A1 | 2/2009 | Jennewine et al. |
| 2009/0055149 A1 | 2/2009 | Hayter et al. |
| 2009/0062633 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0106655 A1* | 4/2009 | Grant .................. G06F 3/03545 715/702 |
| 2009/0112478 A1 | 4/2009 | Mueller, Jr. et al. |
| 2009/0118589 A1 | 5/2009 | Ueshima et al. |
| 2009/0124877 A1 | 5/2009 | Shariati et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Ying et al. |
| 2009/0150186 A1 | 6/2009 | Cohen et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |

(56) References Cited

U.S. PATENT DOCUMENTS

| | | | |
|---|---|---|---|
| 2009/0242425 A1 | 10/2009 | Kamath et al. | |
| 2009/0247855 A1 | 10/2009 | Boock et al. | |
| 2009/0247856 A1 | 10/2009 | Boock et al. | |
| 2009/0247857 A1 | 10/2009 | Harper et al. | |
| 2009/0253973 A1 | 10/2009 | Bashan et al. | |
| 2009/0267765 A1 | 10/2009 | Greene et al. | |
| 2009/0289796 A1 | 11/2009 | Blumberg | |
| 2009/0299155 A1 | 12/2009 | Yang et al. | |
| 2009/0299156 A1 | 12/2009 | Simpson et al. | |
| 2009/0299162 A1 | 12/2009 | Brauker et al. | |
| 2010/0057040 A1 | 3/2010 | Hayter | |
| 2010/0057041 A1 | 3/2010 | Hayter | |
| 2010/0057042 A1 | 3/2010 | Hayter | |
| 2010/0057044 A1 | 3/2010 | Hayter | |
| 2010/0057057 A1 | 3/2010 | Hayter et al. | |
| 2010/0063372 A1 | 3/2010 | Potts et al. | |
| 2010/0141656 A1 | 6/2010 | Krieftewirth | |
| 2010/0160759 A1 | 6/2010 | Celentano et al. | |
| 2010/0168538 A1 | 7/2010 | Keenan et al. | |
| 2010/0168546 A1 | 7/2010 | Kamath et al. | |
| 2010/0174266 A1 | 7/2010 | Estes | |
| 2010/0190435 A1 | 7/2010 | Cook et al. | |
| 2010/0198034 A1* | 8/2010 | Thomas | A61B 5/742 600/365 |
| 2010/0280441 A1 | 11/2010 | Willinska et al. | |
| 2010/0312176 A1 | 12/2010 | Lauer et al. | |
| 2010/0331651 A1* | 12/2010 | Groll | G16H 40/63 345/440 |
| 2011/0004276 A1 | 1/2011 | Blair et al. | |
| 2011/0024043 A1 | 2/2011 | Boock et al. | |
| 2011/0024307 A1 | 2/2011 | Simpson et al. | |
| 2011/0027127 A1 | 2/2011 | Simpson et al. | |
| 2011/0027453 A1 | 2/2011 | Boock et al. | |
| 2011/0027458 A1 | 2/2011 | Boock et al. | |
| 2011/0028815 A1 | 2/2011 | Simpson et al. | |
| 2011/0028816 A1 | 2/2011 | Simpson et al. | |
| 2011/0077490 A1 | 3/2011 | Simpson et al. | |
| 2011/0148905 A1 | 6/2011 | Simmons et al. | |
| 2011/0152637 A1 | 6/2011 | Kateraas et al. | |
| 2011/0208027 A1 | 8/2011 | Wagner et al. | |
| 2011/0208155 A1 | 8/2011 | Palerm et al. | |
| 2011/0320130 A1 | 12/2011 | Valdes et al. | |
| 2012/0078071 A1 | 3/2012 | Bohm et al. | |
| 2012/0108934 A1 | 5/2012 | Valdes et al. | |
| 2012/0165626 A1 | 6/2012 | Irina et al. | |
| 2012/0165640 A1 | 6/2012 | Galley et al. | |
| 2012/0215462 A1 | 8/2012 | Goode et al. | |
| 2013/0035575 A1 | 2/2013 | Mayou et al. | |

FOREIGN PATENT DOCUMENTS

| | | |
|---|---|---|
| EP | 0320109 | 6/1989 |
| EP | 0390390 | 10/1990 |
| EP | 0396788 | 11/1990 |
| EP | 0286118 | 1/1995 |
| EP | 1677668 | 7/2010 |
| WO | WO-2000/059370 | 10/2000 |
| WO | WO-2001/052935 | 7/2001 |
| WO | WO-2001/054753 | 8/2001 |
| WO | WO-2003/082091 | 10/2003 |
| WO | WO-2007/097754 | 8/2007 |
| WO | WO-2008/143943 | 11/2008 |

OTHER PUBLICATIONS

Armour, J. C., et al., "Application of Chronic Intravascular Blood Glucose Sensor in Dogs", Diabetes, vol. 39, 1990, pp. 1519-1526.
Bennion, N., et al., "Alternate Site Glucose Testing: A Crossover Design", Diabetes Technology & Therapeutics, vol. 4, No. 1, 2002, pp. 25-33.
Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, vol. 4624, 2002, pp. 1-10.
Blendea, M. C., et al., "Heart Disease in Diabetic Patients", Current Diabetes Reports, vol. 3, 2003, pp. 223-229.
Brooks, S. L., et al., "Development of an On-Line Glucose Sensor for Fermentation Monitoring", Biosensors, vol. 3, 1987/88, pp. 45-56.
Cass, A. E., et al., "Ferrocene-Medicated Enzyme Electrode for Amperometric Determination of Glucose", Analytical Chemistry, vol. 56, No. 4, 1984, 667-671.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Diabetes Control and Complications Trial Research Group, "The Effect of Intensive Treatment of Diabetes on the Development and Progression of Long-Term Complications in Insulin-Dependent Diabetes Mellitus", New England J. Med., vol. 329, No. 13, 1993, pp. 977-986.
Eckert, B. et al. "Hypoglycaemia leads to an increased QT interval in normal men", Clinical Physiology, vol. 18, No. 6, 1998, pp. 570-575.
Feldman, B., et al., "A Continuous Glucose Sensor Based on Wired EnzymeTM Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Georgescu, B., et al., "Real-Time Multi-model Tracking of Myocardium in Echocardiography Using Robust Information Fusion", Medical Image Computing and Computer-Assisted Intervention, 2004, pp. 777-785.
Goldman, J.M., et al., "Masimo Signal Extraction Pulse Oximetry", Journal of Clinical Monitoring and Computing, vol. 16, No. 7, 2000, pp. 475-483.
Harris, N.D., et al., "Can Changes in QT Interval be used to Predict the Onset of Hypoglycemia in Type 1 Diabetes?," Computers in Cardiology, vol. 27, 2000, pp. 375-378.
Heller, S. R., "Abnormalities of the electrocardiogram during hypoglycemia: the cause of the dead in bed syndrome?," International Journal of Clinical Practice, Suppl. No. 129, 2002, pp. 27-32.
Isermann, R., "Supervision, Fault-Detection and Fault-Diagnosis Methods—An Introduction", Control Engineering Practice, vol. 5, No. 5, 1997, pp. 639-652.
Isermann, R., et al., "Trends in the Application of Model-Based Fault Detection and Diagnosis of Technical Processes", Control Engineering Practice, vol. 5, No. 5, 1997, pp. 709-719.
Johnson, P. C., "Peripheral Circulation", John Wiley & Sons, 1978, pp. 198.
Jones, T. W., et al., "Mild Hypoglycemia and Impairment of Brain Stem and Cortical Evoked Potentials in Healthy Subjects," Diabetes, vol. 39, 1990, pp. 1550-1555.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Landstedt-Hallin, L., et al., "Increased QT dispersion during hypoglycaemia in patients with type 2 diabetes mellitus," Journal of Internal Medicine, vol. 246, 1999, pp. 299-307.
Lortz, J., et al., "What is Bluetooth? We Explain The Newest Short-Range Connectivity Technology", Smart Computing Learning Series, Wireless Computing, vol. 8, Issue 5, 2002, pp. 72-74.
Maher, R. C., "A Method for Extrapolation of Missing Digital Audio Data", Preprints of Papers Presented at the AES Convention, 1993, pp. 1-19.

(56) References Cited

OTHER PUBLICATIONS

Maher, R.C., "Audio Enhancement using Nonlinear Time-Frequency Filtering", AES 26th International Conference, 2005, pp. 1-9.

Malin, S. F., et al., "Noninvasive Prediction of Glucose by Near-Infrared Diffuse Reflectance Spectoscopy", Clinical Chemistry, vol. 45, No. 9, 1999, pp. 1651-1658.

Malmberg, K., "Prospective randomised study of intensive insulin treatment on long-term survival after acute myocardial infarction in patients with diabetes mellitus", British Medical Journal, vol. 314, 1997, pp. 1512-1515.

Markel, A., et al., "Hypoglycaemia-Induced Ischaemic ECG Changes", La Presse Medicale, vol. 23, No. 2, 1994, pp. 78-79.

McGarraugh, G., et al., "Glucose Measurements Using Blood Extracted from the Forearm and the Finger", TheraSense, Inc., 2001, 16 Pages.

McGarraugh, G., et al., "Physiological Influences on Off-Finger Glucose Testing", *Diabetes* Technology & Therapeutics, vol. 3, No. 3, 2001, pp. 367-376.

McKean, B. D., et al., "A Telemetry-Instrumentation System for Chronically Implanted Glucose and Oxygen Sensors", IEEE Transactions on Biomedical Engineering, vol. 35, No. 7, 1988, pp. 526-532.

Okin, P. M., et al., "Electrocardiogramapolarization Complexity and Abnormality Predict All-Cause and Cardiovascular Mortality in Diabetes," Diabetes, vol. 53, 2004, pp. 434-440.

Peterson, K.G., et al., "Regulation of Serum Potassium During Insulin-Induced Hypoglycemia," Diabetes, vol. 31, 1982, pp. 615-617.

Pickup, J., et al., "Implantable Glucose Sensors: Choosing the Appropriate Sensing Strategy", Biosensors, vol. 3, 1987/88, pp. 335-346.

Pickup, J., et al., "In Vivo Molecular Sensing in Diabetes Mellitus: An Implantable Glucose Sensor with Direct Electron Transfer", Diabetologia, vol. 32, 1989, pp. 213-217.

Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", The American Physiological Society, 1995, E155-E161.

Rana, B. S., et al., "Relation of QT Interval Dispersion to the Number of Different Cardiac Abnormalities in Diabetes Mellitus", The American Journal of Cardiology, vol. 90, 2002, pp. 483-487.

Robinson, R. T. C. E., et al. "Changes in cardiac repolarization during clinical episodes of nocturnal hypoglycaemia in adults with Type 1 diabetes," Diabetologia, vol. 47, 2004, pp. 312-315.

Roe, J. N., et al., "Bloodless Glucose Measurements", Critical Review in Therapeutic Drug Carrier Systems, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", Artificial Organs Today, vol. 2, No. 2, 1992, pp. 145-158.

Sakakida, M., et al., "Ferrocene-Mediated Needle-Type Glucose Sensor Covered with Newly Designed Biocompatible Membrane", Sensors and Actuators B, vol. 13-14, 1993, pp. 319-322.

Salehi, C., et al., "A Telemetry-Instrumentation System for Long-Term Implantable Glucose and Oxygen Sensors", Analytical Letters, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.

Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.

Shichiri, M., et al., "Glycaemic Control in Pancreatectomized Dogs with a Wearable Artificial Endocrine Pancreas", Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers", Hormone and Metabolic Research Supplement Series, vol. 20, 1988, pp. 17-20.

Shichiri, M., et al., "Membrane Design for Extending the Long-Life of an Implantable Glucose Sensor", Diabetes Nutrition and Metabolism, vol. 2, 1989, pp. 309-313.

Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", Diabetes Care, vol. 9, No. 3, 1986, pp. 298-301.

Shichiri, M., et al., "Wearable Artificial Endocrine Pancreas With Needle-Type Glucose Sensor", The Lancet, 1982, pp. 1129-1131.

Shults, M. C., et al., "A Telemetry-Instrumentation System for Monitoring Multiple Subcutaneously Implanted Glucose Sensors", IEEE Transactions on Biomedical Engineering, vol. 41, No. 10, 1994, pp. 937-942.

Steinhaus, B. M., et al., "The Information Content of the Cardiac Electrogram at the Stimulus Site," Annual International Conference of the IEEE Engineering in Medicine and Biology Society, vol. 12, No. 2, 1990, pp. 0607-0609.

Sternberg, R., et al., "Study and Development of Multilayer Needle-Type Enzyme-Based Glucose Microsensors", Biosensors, vol. 4, 1988, pp. 27-40.

Thompson, M., et al., "In Vivo Probes: Problems and Perspectives", Clinical Biochemistry, vol. 19, 1986, pp. 255-261.

Turner, A., et al., "Diabetes Mellitus: Biosensors for Research and Management", Biosensors, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117-137.

Velho, G., et al., "Strategies for Calibrating a Subcutaneous Glucose Sensor", Biomedica Biochimica Acta, vol. 48, 1989, pp. 957-964.

Whipple, G., "Low Residual Noise Speech Enhancement Utilizing Time-Frequency", Proceedings of the International Conference on Acoustics, Speech, and Signal Processing, vol. 19, 1994, pp. 15-18.

Wilson, G. S., et al., "Progress Toward the Development of an Implantable Sensor for Glucose", Clinical Chemistry, vol. 38, No. 9, 1992, pp. 1613-1617.

Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517-520.

\* cited by examiner

SYSTEMS, DEVICES AND METHODS FOR MANAGING GLUCOSE LEVELS

RELATED APPLICATIONS

The present application is a continuation of U.S. patent application Ser. No. 17/343,236, filed Jun. 9, 2021, which is a continuation of U.S. patent application Ser. No. 16/128,100, filed Sep. 11, 2018, now U.S. Pat. No. 11,061,491, which is a continuation of U.S. patent application Ser. No. 15/093,010, filed Apr. 7, 2016, now U.S. Pat. No. 10,078,380, which is a continuation of U.S. patent application Ser. No. 13/044,521, filed Mar. 9, 2011, now U.S. Pat. No. 9,326,709, which claims the benefit of U.S. Provisional Patent Application No. 61/312,644, filed Mar. 10, 2010, all of which are incorporated by reference herein in their entireties for all purposes.

BACKGROUND

Individuals with Type 1 diabetes mellitus (T1DM) must periodically administer insulin to sustain their physiological conditions. Some persons with diabetes, other than T1DM patients, might also require administration of insulin. Typically, these patients administer doses of either fast-acting or slow-acting insulin using needle type syringes, for example, prior to meals or exercising, and/or at suitable times throughout the course of each day. The administration of insulin is often performed contemporaneously with the testing of a patient's blood glucose level where such level is measured discretely using fingerstick testing or continuously using an in vivo sensor. If insulin is not appropriately administered, the diabetic patient risks serious damage to the body which may result in death.

Continued developments and improvements in recent years have made infusion device therapy, such as external infusion pump therapy, much more appealing to persons with diabetes due to the added flexibility and freedom it offers and the improvement in regulating and controlling insulin levels on an ongoing basis. The infusion devices, such as external infusion pumps, are typically connected to an infusion set, which includes a cannula, that is placed transcutaneously through the skin of the patient and infusion tubing which fluidly connects the cannula to the infusion device. An insulin infusion device is often used in conjunction with periodic discrete testing by the patient of his or her current glucose levels using an in vitro blood test strip and a blood glucose meter such as the Freestyle® and Precision® blood glucose monitoring systems available from Abbott Diabetes Care Inc., of Alameda, Calif. The infusion device may also be used with a continuous glucose monitoring (CGM) system in which a glucose sensor is transcutaneously positioned in the subcutaneous tissue of a patient, and the continuously monitored glucose levels are transmitted, often wirelessly, from the sensor to a receiver unit by way of a skin-mounted sensor control unit, e.g., the FreeStyle Navigator® continuous glucose monitoring system from Abbott Diabetes Care Inc. The infusion device may be configured to communicate with the CGM system wirelessly or via a wired connection. Alternatively, the infusion device and CGM control unit may be integrated in the same device housing and share user interface mechanisms (i.e., a common display and input keys) and certain functionalities including data storage and processing.

Use of such infusion devices involves the administration of insulin to the patient throughout the day based on pre-programmed patterns, referred to as basal profiles. The basal profiles are generally determined by a physician based on a number of factors, including the patient's insulin sensitivity and other physiological conditions, and are intended to maintain, as accurately as possible, the patient's glucose levels over a predetermined time period. The infusion devices also include databases and computational capabilities to assist the patient in determining if and when additional insulin doses, referred to as bolus doses, are required by the patient. Such dosages include carbohydrate boluses and correction boluses to accommodate for meals and exercise.

The infusion devices and/or analyte monitoring systems typically include a user interface which includes an input mechanism such as buttons and/or a thumb wheel through which the patient may program and control the infusion device. The user interface also typically includes a display which is configured to display digital and graphical information relevant to the patient's infusion progress and the status of various components of the device, as well as other programmable information such as patient-specific basal profiles and bolus doses. In the course of using the analyte monitoring system and the infusion device, data associated with a patient's physiological condition such as monitored analyte levels or insulin dosage information, for example, may be stored and processed. As the complexity of these systems and devices increase, so do the amount of data and information associated with them.

In view of the foregoing, it would be desirable to have a user interface for a diabetes management system or device that provides the user with greater control, functionality, and convenience. It would be additionally advantageous to provide such a user interface, which does not require visual or auditory feedback, to ensure the patient's privacy in managing his or her diabetes.

SUMMARY

The present disclosure provides systems, devices and methods for managing diabetes. An aspect of the present disclosure is the provision of user interface input mechanisms with haptic feedback capabilities to improve the functionality and provide enhanced privacy to a patient when desired.

Glucose management devices of the present disclosure include at least one user interface controlled by a processor in which the user interface has a user input mechanism configured for tactile contact and movement by the user for entering values of parameters for controlling certain functions of the device. The user input mechanism is configured to provide a haptic feedback response to the user as the entered value of a selected parameter approaches a predefined limit or moves away from a preferred value.

With embodiments in which the user interface mechanism is responsive to approaching a predefined limit, the haptic feedback response may be a damping or stiffness of movement of the user input mechanism wherein the extent of damping or stiffness increases the closer the entered value approaches the predefined limit. In certain embodiments, the device may be configured to lock the user input mechanism against further movement upon the entered value exceeding this predefined limit. With embodiments in which the user input mechanism is responsive to moving away from a preferred value for a parameter, the haptic feedback response may provide a spring biasing of the input mechanism toward a centered position defining a preferred value, where the extent of spring bias increases the further the entered value moves away from the predefined preferred value. Alternately or additionally to a change in the intensity or extent of perceived opposing force of the haptic response felt by a user, the haptic feedback response may also provide a detented sensation to the user where one detent corresponds to a predefined unit of the entered value of the selected parameter.

A variety of types of user input mechanisms are suitable for use with embodiments of the present disclosure where the input mechanism provides movement in one, two, three or more degrees of freedom. The type of movement may be linear, rotational, or both, and may have any suitable physical configuration, for example, a button, keypad, knob, dial, thumb wheel, scroll ball, track ball, floating disc, touch screen, etc., to provide the desired type of movement. Movement in any one particular direction may be associated with increasing or decreasing the value of the selected parameter of the glucose management device. The parameter value being entered or changed may also be visually displayed on a screen or display of the user interface, where the displayed digital value is associated with an extent of damping or stiffness of the user input mechanism as a pre-selected limit of the parameter is approached.

The glucose management systems of the present disclosure include at least one glucose management device, such as an insulin infusion pump, a discrete or continuous glucose monitoring device, or an integrated insulin infusion pump and glucose monitoring device, where the device includes one or more user input mechanisms configured to provide a haptic feedback response to a user as described above. With an insulin infusion pump, the various selectable parameters by a user via the user interface mechanism may include any type of bolus dose or basal rate related to the delivery of insulin to a patient, wherein a predefined limit may be a maximum or minimum dosage or rate. With a glucose monitoring device, the selectable parameters may include the patient's measured glucose levels, which may be provided in graphical format on a user interface display including an axis corresponding to time and an axis corresponding to the monitored glucose level wherein movement of the user input mechanism moves a cursor on the display along either or both of the axes.

The present disclosure also includes methods for using the subject systems and devices, as well as methods for infusing an agent or medicament to within a patient, or continuously monitoring selected analyte levels in a patient, or both. One such method provides for managing the level of an analyte within a patient by providing an apparatus or system as described above, moving the user interface input mechanism in a first direction toward a target value of the selected parameter, computing the proximity of the entered parameter value to a predefined or preselected limit of the selected parameter, increasing the stiffness of the input mechanism and changing the displayed value if the entered parameter value is within the predefined limit. The method may further include steps associated with additional features of the haptic response, including for example, locking the input mechanism from further movement if the entered parameter value is equal to the predefined limit, enabling the user to continue to move the input mechanism to change the entered parameter value, enabling the user to change the predefined limit of the selected parameter, moving the user interface input mechanism in a second direction toward a target value of the selected parameter, decreasing the stiffness of the input mechanism when moved in the second direction, and changing the displayed value corresponding to the currently selected value of the parameter. The subject methods, in addition to providing a feedback response, may also include the provision of an audible or visual warning to the user via the user interface.

These and other features, objects and advantages of the present disclosure will become apparent to those persons skilled in the art upon reading the details of embodiments of the present disclosure as described below.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,676,819; 6,730,200; 6,736,957; 6,746,582; 6,749,740; 6,764,581; 6,773,671; 6,881,551; 6,893,545; 6,932,892; 6,932,894; 6,942,518; 7,167,818; and 7,299,082; U.S. Published Application Nos. 2004/0186365, now U.S. Pat. No. 7,811,231; 2005/0182306, now U.S. Pat. No. 8,771,183; 2007/0056858, now U.S. Pat. No. 8,298,389; 2007/0068807, now U.S. Pat. No. 7,846,311; 2007/0227911, now U.S. Pat. No. 7,887,682; 2007/0233013; 2008/0081977, now U.S. Pat. No. 7,618,369; 2008/0161666; and 2009/0054748, now U.S. Pat. No. 7,885,698; U.S. patent application Ser. No. 11/396,135, now U.S. Pat. No. 7,620,438, Ser. Nos. 11/537,984, 12/131,012; 12/242,823, now U.S. Pat. No. 8,219,173; Ser. No. 12/363,712, now U.S. Pat. No. 8,346,335; Ser. Nos. 12/698,124; 12/714,439; 12/807,278; 12/842,013; and Ser. No. 12/848,075, now U.S. Pat. No. 8,478,557.

BRIEF DESCRIPTION OF THE DRAWINGS

A detailed description of various aspects, features and embodiments of the present disclosure is provided herein with reference to the accompanying drawings, which are briefly described below. The drawings are illustrative and are not necessarily drawn to scale, with some components and features being exaggerated for clarity. A reference numeral, letter, and/or symbol that is used in one drawing to refer to a particular element or feature may be used in another drawing to refer to a like element or feature. Included in the drawings are the following.

DETAILED DESCRIPTION

Figure 1:
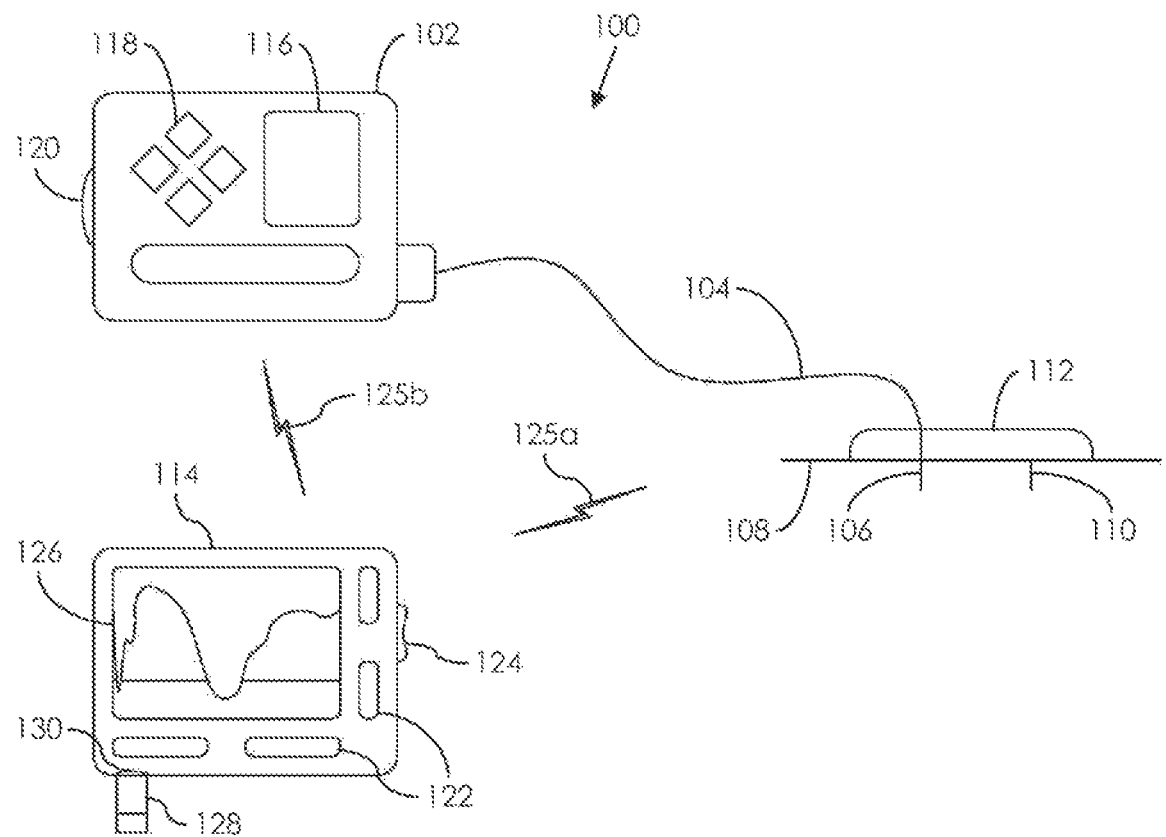
FIG. 1 illustrates one embodiment of a glucose management system of the present disclosure which includes separately housed insulin infusion and analyte monitoring devices.

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates, which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The subject systems, devices and methods of the present disclosure are configured for the management of one or more analyte, such as glucose, levels in the body of a patient. Certain devices include an infusion device or pump for delivering one or more agents, drugs or medicaments to within the body of a patient for maintaining a desired level of the one or more analyte levels. Other devices include a continuous or discrete analyte monitor, or a monitor that is capable of both continuous and discrete monitoring. The systems may include at least one infusion pump or may include complementary devices such as one or more analyte monitoring devices, the functions of which may be housed separately from the infusion device or integrated or housed in a single unit.

Embodiments include implantable or external infusion devices or medication delivery devices that may be controlled or controllable by a separate wireless communication device such as microprocessor driven or controlled devices that are configured for wired or wireless communication with the implantable or external infusion devices. Such infusion devices may also include dedicated control units or features such as user interface buttons and/or actuators integrated with the infusion devices for the control and/or operation of the infusion devices. Furthermore, certain embodiments include on skin patch type infusion devices that are provided or configured with a compact housing and designed for placement on the skin surface of a patient or a user to deliver drug or medication. Exemplary embodiments of infusion devices and systems including the same are provided in U.S. Patent Publication Nos. 2004/0254434, now U.S. Pat. No. 8,460,243, 2006/0224141, 2007/0213657, now U.S. Pat. No. 7,981,034, 2008/0004515, 2008/0103447, now U.S. Pat. No. 8,579,853, 2008/0200897, 2009/0054745, 2009/0054750, now U.S. Pat. No. 8,206,296, 2009/0105658, now U.S. Pat. No. 8,353,881, and 2009/0171269, and others, the disclosures of each of which are incorporated by reference for all purposes.

Due to the prevalence of diabetes, the present disclosure is described and illustrated herein in the context of glucose management in which the agent to be administered is insulin and the analyte to be monitored is glucose; however, the following description is intended to be exemplary of the present disclosure and not limited thereby as the present disclosure may be applied to other applications in which other analytes are monitored and other therapeutic agents are administered to manage those analytes.

Additional analytes that may be monitored by the subject systems include, for example, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Where the monitored drug concentration is that of a therapeutic drug, which may also be that which is being administered by the management system.

Referring now to the figures, FIG. 1 illustrates one embodiment of a glucose management system of the present disclosure which includes separately housed insulin infusion and analyte monitoring devices. Referring to FIG. 1, glucose management system 100 includes an insulin infusion unit 102. The insulin infusion unit 102 utilizes an infusion set for transporting insulin from a reservoir (not shown) housed within the insulin infusion unit 102, transcutaneously into a patient. The infusion set includes infusion tubing 104 for liquid transport of the insulin to a cannula 106 which is configured for transcutaneous placement within a patient. In one embodiment, the systems may be a stand-alone pump including only the insulin infusion unit 102 and the associated infusion set. In other embodiments, the systems may include additional devices which provide additional control in the management of a patient's glucose levels. Referring again to FIG. 1, system 100 also includes an analyte monitoring device 114, which may be configured to continuously monitor a patient's analyte, such as glucose, levels by means of an implantable or in vivo sensor 110 coupled to a sensor control unit 112 mounted to the patient's skin by way of an adhesive patch 108. Analyte monitoring unit 114 is configured to wirelessly receive signals associated with analyte levels detected by the analyte sensor 110 which are periodically and/or intermittently received by the analyte monitoring unit 114 from sensor control unit 112 over communication path 125a. Analyte monitoring unit 114 may be configured to include a transceiver unit (not shown) for bidirectional communication over the communication path 125a, or in certain embodiments may include radio frequency identification (RFID) components for, e.g., passive or active RFID systems, and sensor control unit 112 may likewise be configured to include RFID components to communicate with an RFID-enabled analyte monitoring unit 114.

In other embodiments, analyte monitoring unit 114 may be configured for discrete monitoring of analyte levels by the use of an in vitro test strip 128 with analyte sample provided thereon, which is receivable at a port 130 within the housing of analyte monitoring unit 114. In yet another configuration, as shown in FIG. 1, analyte monitoring unit 114 is designed for both continuous and discrete monitoring of analyte levels by means of a transcutaneous in vivo sensor 110 and in vitro test strip 128, respectively. In any of the aforementioned configurations, the analyte monitoring unit 114 may be configured to communicate unidirectionally or bidirectionally with insulin infusion unit 102 over communication path 125b, which may be a wireless or wired connection.

Examples of continuous monitoring systems and discrete analyte monitoring systems and data management systems that may be employed can be found in U.S. Pat. Nos. 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; and 7,811,231, and elsewhere, the disclosures of each which are incorporated herein by reference for all purposes.

Figure 2:
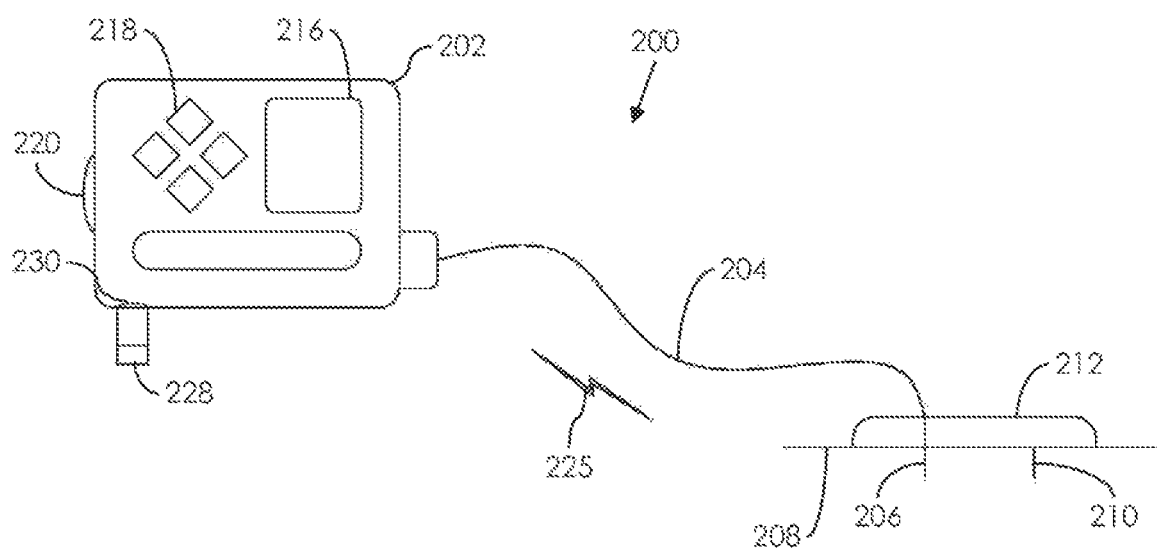
FIG. 2 illustrates another embodiment of a glucose management system of the present disclosure which provides insulin infusion and analyte monitoring devices housed in the same unit.

FIG. 2 shows another glucose management system 200 of the present disclosure in which the insulin infusion and analyte monitoring devices are integrated into a single integrated infusion and monitoring device 202. By providing many of the information associated with analyte, such as glucose, levels and insulin infusion information in one integrated infusion and monitoring device 202, the patient may be provided with the additional convenience and discreteness in managing diabetes and improving insulin therapy. The integrated infusion and monitoring device 202 houses an insulin reservoir (not shown) which is coupled to an infusion tubing 204 connected to a cannula 206 which is configured for transcutaneous placement through a skin layer of a patient. Integrated infusion and monitoring device 202 may be configured to communicate unidirectionally or bidirectionally with a sensor control unit 212 over a communication path 225, which may be a wireless connection, or a wired connection provided via direct coupling between the two components by means of a cable (not shown). The sensor control unit 212, which is in electrical contact with an in vivo analyte sensor 210 subcutaneously positioned under the skin of the patient, is retained in position by an adhesive layer or patch 208 provided on the bottom surface of the sensor control unit 212. Integrated infusion and monitoring device 202 may also be configured for discrete monitoring of glucose levels by means of in vitro test strip 228 with analyte sample provided thereon and received at a test port 230 in the housing of the integrated infusion and monitoring device 202.

The communication paths 125a, 225 between the respective sensor control units 112, 212 and the respective analyte monitoring unit 114 or integrated infusion and monitoring device 202, respectively of FIGS. 1 and 2, as well as the communication path 125b between the analyte monitoring unit 114 and insulin infusion unit 102 of FIG. 1, may include a radio frequency (RF) communication link, WiFi communication link, Bluetooth® communication link, infrared (IR) communication link, RFID communication link, or any other type of suitable wireless communication link or protocol between two or more electronic devices. Alternatively, the various data communication links may be a wired cable connection such as, for example, but not limited to, an RS-232 connection, universal serial bus (USB) connection, or serial cable connection.

The analyte monitoring unit 114 or the insulin infusion device 102 of FIG. 1, or both, and the integrated infusion and monitoring device 202 of FIG. 2 may be configured to further communicate with a data processing terminal (not shown) which may include a desktop computer terminal, a data communication enabled kiosk, a laptop computer, a handheld computing device such as a personal digital assistant (PDA), or a data communication enabled mobile telephone, and the like, each of which may be configured for data communication via a wired or a wireless connection. A data processing terminal may include a physician's terminal and/or a bedside terminal in a hospital or home environment, for example.

With each of the embodiments of FIGS. 1 and 2, the respective infusion cannulas 106, 206 and infusion tubing 104, 204 are coupled through the control unit 112, 212 and the adhesive patch 108, 208 to minimize the area of the skin occupied by the system components. However, the infusion components (i.e., cannula and infusion tubing) may be transcutaneously positioned at a distance away from the monitoring components (transmitter and sensor) or even on different areas of the body, in which case two separate patches may be used. In the illustrated embodiments, the respective control unit, in vivo sensor and cannula may be configured to be positioned simultaneously, or the sensor and cannula may be configured to be placed first with the control unit then mounted over and in electrical contact with the sensor. In another embodiment, the control unit may be mounted first and configured to receive the cannula and/or the sensor and facilitate positioning of the cannula and/or sensor through the skin of the patient. The infusion tubing may be configured to operatively couple with a port (not shown) within the housing of the respective control units so as to be in fluid alignment with the cannula and to provide a substantially fluid-tight seal between the tubing and cannula.

Each of the insulin infusion unit 102 and analyte monitoring unit 114 of FIG. 1 and the integrated infusion and analyte monitoring device 202 of FIG. 2 have one or more processors (e.g., application specific integrated circuits (ASICs), microprocessors, etc.) or control units (not shown) which are configured to perform data storage and processing based on one or more preprogrammed or predetermined processes. For example, a processor of analyte monitoring unit 114 of FIG. 1 or an analyte monitoring processor of integrated infusion and analyte monitoring device 202 of FIG. 2 may be configured to store the received signals associated with analyte levels in a data storage unit, such as a memory (not shown). Alternatively or additionally, the processor may be configured to process the signals associated with the analyte levels to generate trend indication by, for example, display of a line chart or an angular icon based display for visual output on display 126 (FIG. 1), 216 (FIG. 2). In certain embodiments, a processor is programmed to determine the rate of change of an analyte and/or the rate of the rate of change of an analyte over time based on current and historical analyte information obtained from the sensor 110, 210 via the control unit 112, 212 and stored in a memory. Additional information which may be processed, stored and displayed by the analyte monitor includes, but is not limited to, the substantially contemporaneous and real time analyte levels of the patient received from respective control unit 112, 212 as detected by the respective sensor 110, 210. The real time analyte level may be displayed in a numeric format or in any other suitable format which provides the patient with the accurate measurement of the substantially real time analyte level detected by the sensor.

The processor of insulin infusion unit 102 or an infusion-specific processor within integrated infusion and analyte monitoring device 202 may include capabilities for programming basal profiles and for calculating bolus doses including, but not limited to, correction boluses, carbohydrate boluses, extended boluses, and dual boluses, which may be based on one or more factors including the patient's insulin sensitivity, insulin on board, intended carbohydrate intake (for example, for the carbohydrate bolus calculation prior to a meal), the patient's measured or detected glucose level, and the patient's glucose trend information. Such calculations may be performed by the patient using the user interface (UI) displays 116, 216 and keypads 118, 218 of insulin infusion unit 102 and integrated infusion and analyte monitoring device 202, respectively. In a further variation of system 100 of FIG. 1, the bolus calculation capabilities may also be provided in the analyte monitor unit 114.

In each of the system embodiments, the individual functional units, i.e., the insulin infusion unit 102 of system 100 (FIG. 1), the analyte monitoring unit 114 of system 100 and the integrated infusion and analyte monitoring device 202 of system 200 (FIG. 2), are configured with a substantially compact housing that can be easily carried by the patient or conveniently worn on the patient's clothing (for example, housed in a holster or a carrying device worn or clipped to the patient's belt or other parts of the clothing). As mentioned earlier, each unit or only some units of the system may include a user interface (UI) on the housing for outputting information to the user or patient and inputting information by the user or patient.

Output mechanisms include a visual output, such as displays 116, 126 (FIG. 1) and 216 (FIG. 2), which may be configured to display digital data and/or graphical and/or analog data. Other output mechanisms may include one or more audio output devices such as speakers or buzzers (not shown) integrated with the device housings so as to output audible alerts or alarms based on the occurrence of one or more predetermined conditions associated with insulin infusion unit 102, analyte monitoring unit 114 or integrated infusion and analyte monitoring device 202. For example, insulin infusion unit 102 may be configured to output an audible alarm or alert to the patient upon detection of an occlusion in the infusion tubing 104 or upon the occurrence of a timed event such as a reminder to prime the infusion tubing 104 upon replacement of the cannula 106, and the like. Analyte monitoring unit 114 may similarly be configured to output an audible alarm or alert when a predetermined condition or a pre-programmed event occurs, such as, for example, a reminder to replace sensor 110 after its useful life (e.g., of 3 days, 5 days, 7 days, 10 days, 14 days or more), or one or more alerts associated with the data received from the sensor control unit 112 corresponding to the patient's monitored analyte levels. Such alerts or alarms may include a warning alert to the patient when the detected analyte level is beyond a predetermined threshold level or when the trend of the detected analyte levels within a given time period is indicative of a significant condition, such as potential hyperglycemia or hypoglycemia, which require attention or corrective action. The audible alarms may be output alone or in combination with one or more visual alerts such as an output on the display units 116, 126 (FIG. 1) or 216 (FIG. 2), or with a vibratory alert which would provide a tactile indication to the patient of the associated alarm and/or alert. Accordingly, alarms and/or alerts may be audible and/or visual and/or tactile.

Referring still to FIGS. 1 and 2, user interface input mechanisms may include one or more of keypads 118, 218, buttons 122, 124 and thumb wheels or jog dials 120, 220, as well as displays 116, 126 and 216 where the displays may be touch screens. The interface inputs may be used by the user/patient to input data, select menus, and perform the various bolus calculations discussed above. With a stand-alone pump, the patient may have to key in real-time glucose levels (as well as other information) obtained by discrete testing or by a continuous monitor not in automatic communication with the pump. On the other hand, the glucose management system 100 of FIG. 1 and the glucose management system 200 of FIG. 2 provide enhanced functionality by having substantially continuous real time glucose data and trend information automatically provided to the infusion device/processor by the continuous analyte monitoring device/process. Accordingly, bolus doses of insulin are more easily quantified, and the pre-programmed basal profiles are more easily adjusted by the patient.

Embodiments of the user interface input elements of the present disclosure are configured to provide force (kinesthetic) feedback and/or tactile feedback to the user in response to an activating motion or input, e.g., pressing a button or rotating a jog dial, by the user. These feedbacks are collectively referred to herein as "haptic feedback." Haptic technology or haptics takes advantage of a user's sense of touch by applying forces, vibrations, and/or motions upon the user which is felt as a physical sensation to the touch, typically in response to a user-initiated action or motion. Accordingly, embodiments of the subject systems include haptic feedback so that the physical sensation is felt by the user manipulating an input unit of the interface device, such as a joystick, a mouse button, etc., used to control the system. One or more motors or other actuators controlled by the computer system are coupled to the input unit. The computer controls forces on the input unit and/or device housing in conjunction and coordinated with displayed events and interactions by sending control signals or commands to the actuators. The computer system thus conveys physical force sensations to the user in conjunction with other supplied feedback as the user is grasping or contacting the input unit.

Certain embodiments of haptic feedback use electromagnetic technologies such as vibratory motors, such as the pager motor or voice coils, in which an offset mass is moved by a magnetic field. The electromagnetic motors typically operate at a resonance frequency and provide strong feedback, but have limited range of sensations. Other actuator technologies which offer a wider range of effects and more rapid response times include electroactive polymers, piezoelectrics, and electrostatic surface actuation. Electroactive polymers or EAPs are polymers whose shape is modified when a voltage is applied to them. Piezoelectricity is the ability of some materials (notably crystals and certain ceramics) to generate an electric field or electric potential in response to applied mechanical stress. The effect is closely related to a change of polarization density within the material's volume. Electrostatics involves the buildup of charge on the surface of objects due to contact with other surfaces. When at least one of the surfaces has a high resistance to electrical flow, the effects of charge exchange are usually noticeable. This is because the charges that transfer to or from the highly resistive surface are more or less trapped there for a long enough time for their effects to be observed.

Figure 3:
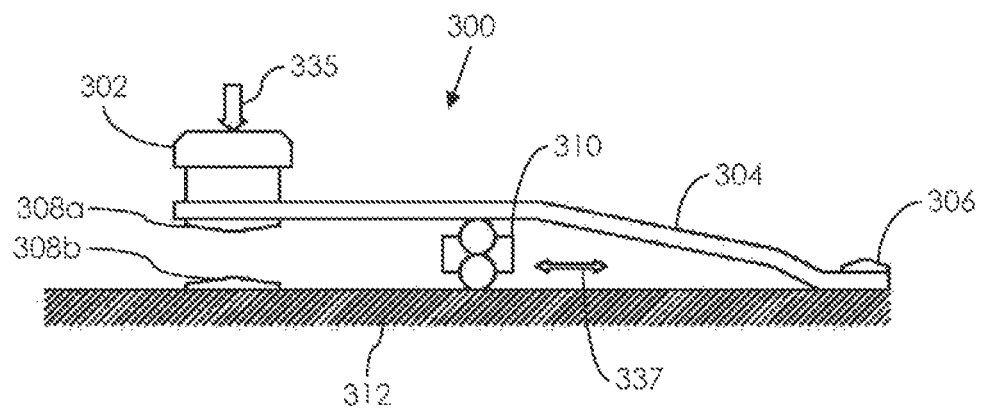
FIG. 3 is a schematic illustration of a haptic feedback-enabled switch or actuator for application in the user interface (UI) input mechanisms in certain embodiments.

Other embodiments use the active elements such as motors or piezoactuators to alter the passive mechanical property in the path of the human interface. One example is to alter the effective pivot point of a flexible cantilever that provides stiffness and/or damping to a mechanical switch. FIG. 3 illustrates a schematic representation of such a haptic feedback-enabled switch 300, the functional principles of which are suitable for use for certain user interface input applications of the present disclosure and may be implemented by any of the aforementioned haptic technologies. Switch 300 includes a button 302 positioned on the free end of a cantilever 304 secured to a ground reference 312 at a fixed or pivot end 306. A first electrical contact 308a is provided on the underside of cantilevered button 302 and a second electrical contact 308b is provided on the ground reference 312 opposite to and in alignment with electrical contact 308a. When the two contacts 308a, 308b meet, the switch is closed, effecting an action, e.g., incremental increase or decrease of a value or quantity, selection of a specific value or range of values, scrolling of a cursor, etc. A double-roller mechanism 310 is frictionally engaged between the underside of cantilever 304 and ground 312 and is configured to translate linearly along the length of cantilever 304 between fixed or pivot end 306 of the cantilever and electrical contacts 308a, 308b, as shown by arrow 337. Linear movement of mechanism 310 is controlled by an actuator mechanism (not shown). Upon application of a downward force 335 on button 302 in order to establish physical contact between the electrical contacts 308a, 308b, (in addition to the resulting action identified above) the actuator may be incrementally activated to incrementally move double-roller mechanism 310 closer to or farther away from button 302. Movement of mechanism 310 closer towards button 302 increases the responsive stiffness felt by the user pressing on button 302, and movement away from button 302 decreases the stiffness felt by the user. The increasing stiffness felt by the user, for example, may indicate relative advancement to a fixed threshold. In one variation, when double-roller mechanism 310 is moved toward button 302 and reaches some specified lateral distance from button 302 or is placed directly between the electrical contacts 308a, 308b, it provides a hard stop where the button can no longer be pressed and/or the electrical contacts will no longer be able to touch each other, indicating that a threshold limit has been reached.

Figure 4A:
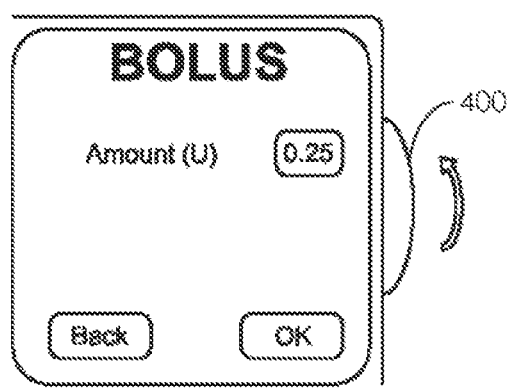
FIGS. 4A-4C illustrate exemplary user interface (UI) input mechanisms usable with the control devices of the systems in certain embodiments.
Figure 4B:
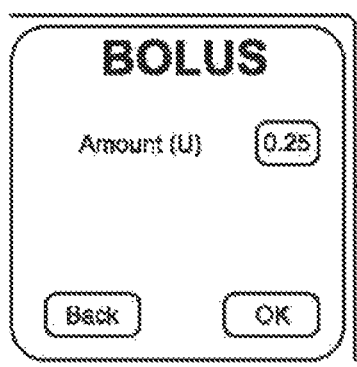
Figure 4C:
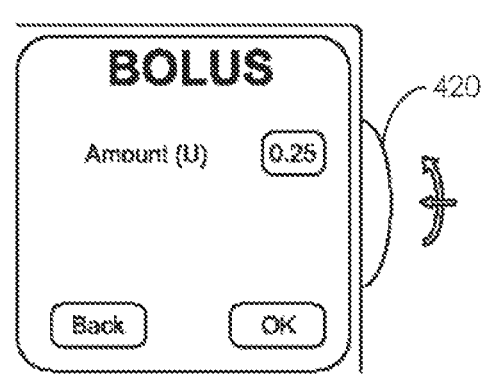

The switch of FIG. 3 is merely intended to be a simple schematic example of how a haptic feedback mechanism works. For purposes of the present disclosure, however, user interface input mechanisms may include, but are not limited to, buttons, keypads, knobs, dials, thumb wheels, scroll balls, touch screens, etc. integrated with the housing of a glucose management device, such as an insulin infusion unit, analyte monitoring unit, or a unit integrating control of insulin infusion and analyte monitoring. The input mechanisms may be a continuous one degree-of-freedom type, as shown in FIG. 4A, e.g., the dial 400 can be rotated continuously. Alternatively, the input mechanism may have one degree-of-freedom but enable binary movement in which it can be moved in two, usually opposite, directions, e.g., as shown in FIG. 4B, button 410 can be toggled in two directions. A multi-directional mechanism, such as a scroll ball, track ball or floating disc, usually providing movement with three or four degrees-of-freedom, may also be employed. Certain mechanisms may provide more than one type of input motion. For example, as shown in FIG. 4C, a jog wheel 420 may be configured to be depressed like a button in addition to being rotatable about an axis.

The amount of responsive force of the haptic feedback may be the same regardless of the number of depressions or the extent of travel of an input mechanism, where one level, value or point of adjustment is met by the equivalent physical sensation of a "click", such as riding over a detent or the like. The "resolution" or magnitude of such detents may be predefined or variable. One useful application for a detent-action input mechanism is for providing user feedback upon the user-initiated incrementing or decrementing of a value, with or without threshold or safety limits, where movement of the input mechanism in one direction increments a value, for example, of a dose of a medicament to be administered to a patient, and movement in a second direction decrements the value of that dose.

Alternatively or additionally, the haptic feedback sensation may be one of a gradual stiffening of the input mechanism such that continued movement of it by the user in one direction is met with greater and greater resistance to prevent an input error hazard and to make the user more aware of certain safety-based limits. For example, if a jog wheel or scroll ball input mechanism is used, the ability of the wheel or ball to roll freely given a certain "spin" will diminish as the selected value nears a threshold or safety limits. This can be achieved by coupling the jog wheel or scroll ball about its axis of rotation, i.e., at its axle, to a motor which outputs a torque on the axle in a direction opposite to the motion of the axle and in an amount which increases proportionately as the axial velocity of the wheel or ball increases.

Where a model-based system is employed which provides for a preferred or target value for certain parameters, the UI input mechanism may be spring-biased toward a "center" position representative of the preferred or target value. When the input mechanism, such as a jog wheel or roller ball, is rotated or spun away from this default center position, the wheel or ball will slowly or gradually return to the default position. This haptic effect may be implemented by connecting the wheel or ball's axle to a motor. The amount of torque exerted on the axle is configured to increase proportionately as the axle deviates from the default position in either or any direction, thereby acting as a virtual spring. Alternatively, the virtual spring effect may be configured to keep the input mechanism within a preferred or acceptable range of motion rather than a discrete center position. Still yet, there may be two or more such center positions which correspond to favorite or commonly used user settings, which, for example, may correspond to typical carbohydrate boluses to be administered for breakfast, lunch, dinner and snacks, respectively.

The haptic response of the input mechanisms of embodiments of the present disclosure may have any one or more of the following features: (1) the input mechanism provides tactile feedback simulating discrete detents where one detent corresponds to a predefined unit, typically a single unit, of the value of a given user-modifiable or user-selected parameter; (2) the apparent damping or resistance of the mechanism's movement (whether a gradual rotation of a wheel or an incremental or stepped input of a button) increases as a limit is approached—a virtual damper mechanism; (3) upon being advanced to a position or being depressed a number of times beyond a set limit, the mechanism's apparent resistance or stiffness causes it to return to a position representing the closest allowable value of the parameter being adjusted; (4) with or without gradual or incremental resistance, when advanced beyond a position or point representing a set limit, travel of the mechanism ceases or is locked altogether; and (5) the input mechanism is physically biased toward one or more discrete positions or to within a range of acceptable movement rather than having or in addition to having set limits—a virtual spring mechanism. The input mechanisms may be further configured to unlock the user input mechanism and/or cease further haptic responses if the user activates an override of the set limits or otherwise conforms to within the currently-set limitations.

Unlike a system having only absolute hard limits on its parameters (which in some cases is absolutely necessary), a system having modifiable parameters allows use of a dynamic range limit that may be modified for reasons specific to a particular user or to accommodate an urgent exception. Haptic feedback capability enables a more dynamic user interface for a system in which certain parameters, and in some cases, limits on parameter ranges, may be user-modified. In the context of the user interface input (UI) mechanisms of the subject diabetic management systems of the present disclosure, haptic feedback capabilities, in addition to enhancing usability, are provided to prevent hazardous outcomes, such as under- or overdosing, which may be caused by user error. Various haptic applications include, but are not limited to, insulin delivery threshold settings, i.e., maximum or minimum thresholds, being approached or achieved upon user "request of" or input to an infusion pump. More specifically, when a user's input, via a user interface (UI) input mechanism configured with haptic feedback, either to affect a change in basal rate or for the administration of one or more bolus doses, approaches or attempts to surpass or override a pre-defined maximum (or minimum) volume of insulin already delivered or to be delivered by an insulin pump, the input mechanism provides a resistive or opposite force which may increase or decrease in some sort of linear fashion as the quantity of insulin selected by the user increases or decreases, respectively.

Figure 5:
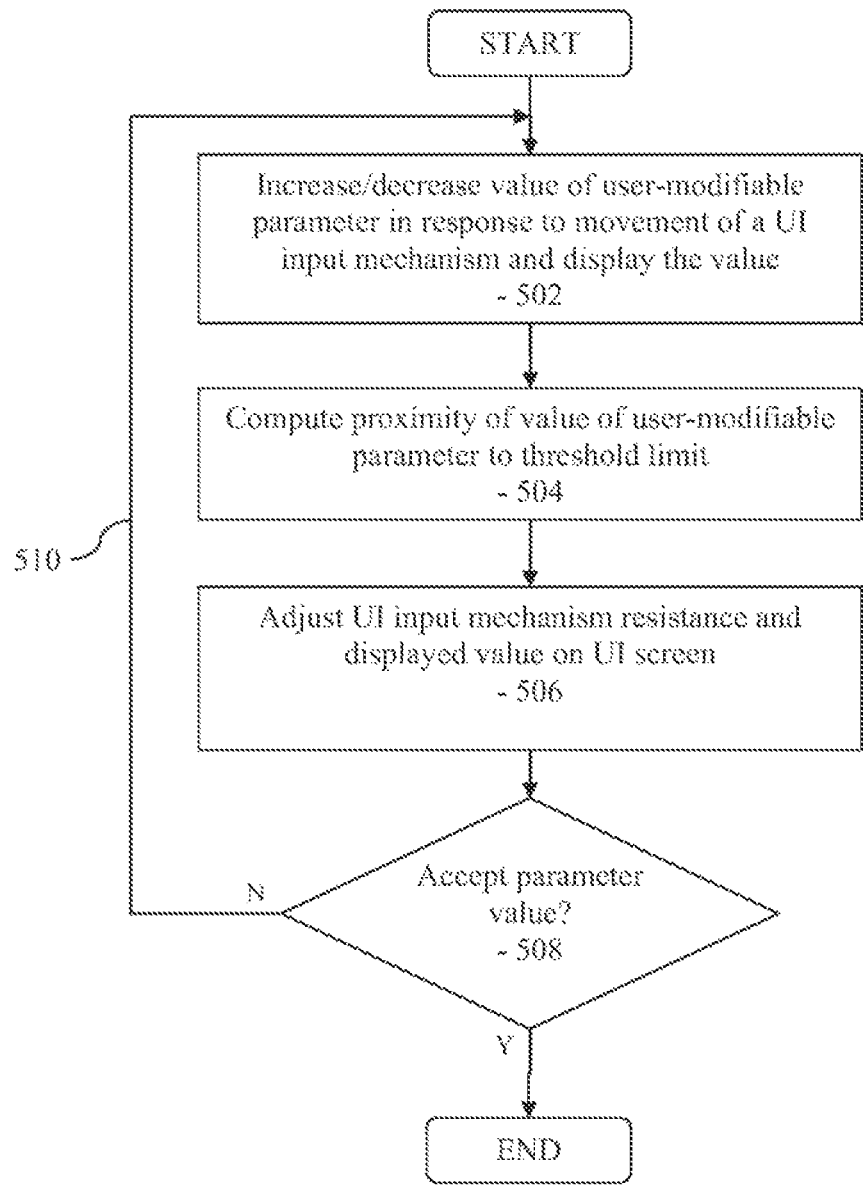
FIG. 5 is a flow chart illustrating an exemplary process of haptic feedback implementable by the systems and devices of the present disclosure.

A flow chart of the above process is illustrated in FIG. 5. Referring to FIG. 5, upon deciding to increase/decrease user-modifiable value, e.g., the volume of a bolus dose of insulin, the user moves, e.g., presses, spins, rolls, etc., a UI input mechanism (502), e.g., a button, wheel, roller ball, etc., presented on the housing of an insulin infusion device one or more times or detents to adjust a digital value of the parameter being adjusted (incremented or decremented), e.g., to increase a bolus dose to be delivered, which value is also presented on the pump's UI display. For each incremental movement of the UI input mechanism, i.e., for each press of the button, a processor within the control system, e.g., infusion device, computes the proximity of the user requested value, e.g., bolus volume, to a predefined or a dynamically computed threshold limit (504), which limit may be based on one or more parameters including, for the bolus dose example, the total daily dosage (TDD) entered by the user, recent bolus history, the preset basal rate, carbohydrate intake, exercise events, etc. The processor then activates an actuator or the like which adjusts the tactile resistance, e.g., stiffness, of the user interface mechanism (506) to reflect the relative proximity of the requested bolus dose value to the predefined or computed limit. The processor also then, substantially simultaneously, adjusts the digital value of the requested value, e.g., bolus dose, on the UI display (506). If the adjusted bolus amount is acceptable to the user, the user may be required to further acknowledge such by depressing the same or another user interface mechanism (508), and the haptic response cycle is ended. If the process is not acceptable to the user (508) the process is repeated (510) for each increment/decrement of the UI input mechanism and, without any automatic locks provided by the system, may allow the user to override the predefined limits by further movement of the UI input mechanism.

Figure 6:
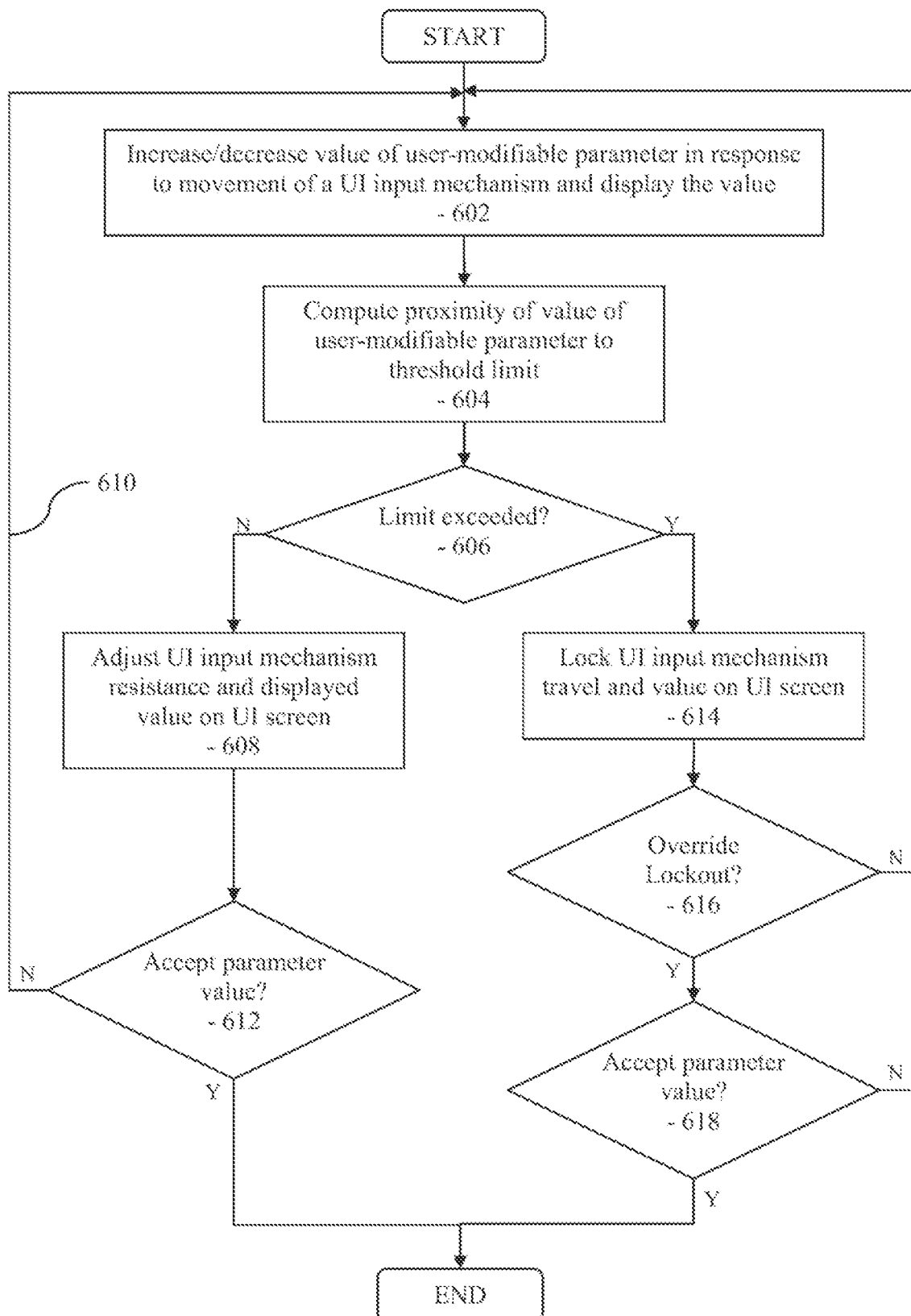
FIG. 6 is a flow chart illustrating another exemplary process of haptic feedback implementable by the systems and devices of the present disclosure.

In another embodiment, as illustrated in FIG. 6, a process may be configured with automatic safety lockouts where continued movement of the UI mechanism by the user results in a hard stop in which further movement of the UI mechanism is impossible without overriding the system, for example, when a pre-defined insulin threshold has been met or exceeded. The initial steps of moving the UI mechanism (602) to achieve a desired parameter value, e.g., bolus dose, and computing the proximity of the incremented/decremented parameter value (604), e.g., bolus dose, to a predefined or a dynamically computed limit are substantially the same as for the process of FIG. 5. If the selected parameter value, e.g., bolus dose, does not exceed the predefined or preselected limit (606), the UI input mechanism resistance, e.g., button stiffness, and the corresponding digital value in the UI display are each adjusted accordingly (608). At this point, the user may accept the last selected, non-limit-exceeding amount (612) or may attempt to further increment/decremented the selected parameter value (610), e.g., the selected bolus dose amount. However, should the selected parameter value, e.g., bolus dose, exceed the predefined limit (606), the processor may activate an actuator or the like to lock UI input mechanism travel, and the digital value of the previously selected, non-exceeding parameter value, e.g., bolus dose amount, will remain on the UI display screen (614). It is noted that with the input mechanism lockout feature (614) to ensure against a hazardous dosing situation or the like, it may not be necessary for the UI mechanism to have an adjustable tactile resistance feature. Upon lockout (614) the user may have the option to override the lockout (616). The system, via the user interface, may be configured to provide an audible or visual warning to the user, or a textual notice to the user of the risk of overriding the lockout (if such an override is available) or requesting the user to redefine the safety or threshold limits in the case where one or more of the user-entered parameters (but not system-based or physician-set parameters) is/are allowed to be adjusted. Should the acceptable range of the parameter be increased or decreased, the resulting range of resistance, stiffness or damping will also be increased or decreased, respectively. It is noted that adjusting one such parameter may in turn require other parameter or parameter ranges to be adjusted. The system may be configured to automatically adjust such other dependent parameters or otherwise notify the user of the need to adjust such. Once the parameter threshold(s) are redefined, the user may re-enter or re-select the desired parameter value using the UI input mechanism (i.e., repeating or redoing the parameter entry process) (618). Otherwise, the lockout may continue until the user selects a non-limit-exceeding value of the selected parameter by decrementing/incrementing (as the case may be) the currently-displayed, over-limit parameter value (618) (i.e., repeating the parameter entry process), cancels the operation, or manually overrides the system (616) if the system is configured to allow such an override.

Other aspects of diabetes management devices and systems which involve user input in which haptic feedback capabilities are suitable or useful include, but are not limited to, CGM graphical applications in which a user-controlled cursor is scrollable over the respective graph axes. For example, a UI input dial may be employed to scroll a cursor along the time-based axis (e.g., the x-axis) of the graph wherein detent sensations are provided when certain pre-programmed events, e.g. meals and exercise, are passed. The system may be further configured such that the dial's resistance increases along the time-based axis as the cursor approaches glucose values representative of hypoglycemic or hyperglycemic limits. Additionally or alternatively, the extent of resistance or stiffness of the jog wheel may be relatively associated with rising and falling glucose levels. Additionally or alternatively, movement of an input mechanism may correspond to movement of a cursor along the axis representing glucose level (e.g., the y-axis), wherein detent sensations are provided at each unit change, i.e., increase or decrease, in glucose level.

In certain embodiments, the diabetes management device may include an analyte monitoring device, such as a glucose monitoring device, including a discrete or continuous glucose monitoring device, which may be used in conjunction with or independently from a medication infusion device, such as an insulin pump. The analyte monitoring device may be configured to include a user interface (UI) including selectable menu parameters. Such parameters may include selectable or adjustable thresholds and intervals, such as, but not limited to, a time interval between analyte, such as glucose, check reminders, thresholds for high and/or low glucose level alerts, the projection time for projected high and/or low glucose level alerts, and other parameters associated with a patient's needs. Parameters including scheduling parameters, threshold levels, and UI personalized configurations may be selectable or adjustable based on the patient's particular medical condition, such as, for example, louder alarms, lower hyperglycemic threshold levels, or larger display preferences for patients with advanced medical conditions effecting the patient's sight, hearing, or other medical and health conditions. Similar to the haptic feedback embodiments described above associated with an infusion device, the user interface of the analyte monitoring device may be configured such that actuation of the user interface, such as buttons, wheels, or the like, may increase in perceived stiffness as the selected parameters approach a programmed or chosen limit. In other aspects, selection through menu choices or available parameter values may be associated with simulated discrete detents where one detent corresponds to a predefined unit or menu choice.

The user interface mechanisms of the present disclosure may be configured wherein haptic-type feedback may be the only form of user feedback or the haptic feedback may be complemented by another form of feedback such as audio feedback, e.g., a buzzing noise or pinging sound from a speaker on the user interface, visual feedback, e.g., a flashing light, a change in color or a blinking symbol on the user interface display, or another type of tactile feedback such as a vibration of the user interface or device housing. Where discreteness or silence is necessary or desired (such as when in a meeting or at the movies), a haptic-only feedback response will allow a user to make adjustments to parameters without needing to see or hear the UI device and, as such, the user is able to manipulate the device while the device is kept concealed within a pocket or on a belt loop.

One aspect of the present disclosure includes a glucose management device having a processor and a user interface controlled by the processor comprising a user input mechanism configured for tactile contact and movement by a user for entering values of one or more parameters for controlling the glucose management device, wherein the user input mechanism is configured to provide a haptic feedback response to the user as the entered value of a selected parameter approaches a predefined limit.

In one embodiment, the haptic feedback response comprises a damping of movement of the user input mechanism wherein the extent of damping increases the closer the entered value approaches the predefined limit.

In a further embodiment, the haptic feedback response further comprises locking the user input mechanism against further movement upon the entered value of the selected parameter exceeding the predefined limit.

In another embodiment, the user input mechanism is movable in at least two directions wherein movement in a first direction increases the value of the selected parameter and movement in a second direction decreases the value of the selected parameter.

In a further embodiment, the user input mechanism is rotatable about an axis and the movement of the user input mechanism is rotational.

In yet a further embodiment, the user input mechanism is further moveable in a linear direction transverse to the axis of rotation.

The user input mechanism is a toggle button in other embodiments.

In another embodiment, the user interface comprises a display for displaying the values of the one or more parameters for controlling the glucose management device, wherein the display is configured to display the entered value of the selected parameter.

In a further embodiment the display is configured to provide visual feedback to the user when the entered value of the selected parameter exceeds the predefined limit.

In other embodiments, the haptic feedback response further comprises providing a detented sensation to the user wherein one detent corresponds to a predefined unit of the entered value of the selected parameter.

Another aspect includes a glucose management device having a processor, and a user interface controlled by the processor comprising a user input mechanism configured for tactile contact and movement by a user for entering values of one or more parameters for controlling the glucose management device, wherein the user input mechanism is configured to provide a haptic feedback response to the user as the entered value of a selected parameter moves away from at least one predefined preferred value for the selected parameter.

In one embodiment, the haptic feedback response comprises a spring biased movement of the user input mechanism toward a centered position corresponding to the at least one predefined preferred value.

In a further embodiment, the extent of spring bias increases the further the entered value of the selected parameter moves away from the at least one predefined preferred value.

In another embodiment, the user input mechanism is rotatable in at least two directions.

In one embodiment, the user input mechanism is one or more of a dial, knob, scroll ball, track ball and floating disc.

Another aspect includes a glucose management system having an insulin infusion device comprising a user interface controlled by at least one processor, the user interface comprising a user input mechanism configured for tactile contact by a user for entering values of one or more parameters for controlling, at least in part, the infusion of insulin to a patient, wherein the user input mechanism is configured to provide a haptic feedback response to the user as the entered value of a selected parameter approaches a predefined limit.

In one embodiment, the selected parameter of the system is the bolus dosing of insulin, and wherein the predefined limit is a maximum bolus dose.

In another embodiment, the user input mechanism comprises at least one of a button, keypad, knob, dial, thumb wheel, scroll ball, floating disc or touch screen.

Another aspect includes a glucose monitoring device in communication with the insulin infusion device.

In one embodiment, the glucose monitoring device provides discrete, continuous or both discrete and continuous measurement of the patient's glucose level.

In certain embodiments, the insulin infusion device and the glucose monitoring device are provided within the same housing, and the user interface is further configured for entering values of parameters for controlling, at least in part, the monitoring of glucose levels of the patient.

In yet another aspect, a glucose management system having a glucose monitoring device including a user interface controlled by at least one processor, the user interface comprising a display for displaying glucose levels of a patient and a user input mechanism configured for tactile contact by a user for evaluating displayed glucose levels, wherein the user input mechanism is configured to provide a haptic feedback response to the user as a monitored glucose level approaches a predefined limit is provided.

In one embodiment, the displayed glucose levels are provided in graphical format comprising an axis corresponding to time and an axis corresponding to the monitored glucose level and wherein movement of the user input mechanism moves a cursor on the display along the axis corresponding to time.

In other embodiments, the predefined limit comprises a hypoglycemic level, a hyperglycemic level, or both.

In certain embodiments, the glucose monitoring device monitors glucose continuously.

In one aspect, the glucose monitoring device and the insulin infusion device are provided within the same housing, and the user interface is further configured for entering values of parameters for controlling, at least in part, the infusion of insulin to the patient.

Another aspect of the present disclosure includes a method for managing the level of an analyte of a patient including providing an apparatus for managing the level of an analyte of a patient comprising a processor and a user interface controlled by the processor, the user interface comprising a user input mechanism configured for tactile contact and movement by the user for entering values of one or more parameters for controlling the apparatus, wherein movement of the input mechanism changes the value of a selected parameter, and a display for displaying values of the one or more parameters for controlling the apparatus, wherein the display is configured to display digital values corresponding to the user-entered values of the selected parameter, displaying a digital value on the display corresponding to the current value of the selected parameter, moving the user interface input mechanism in a first direction toward a target value of the selected parameter, computing the proximity of the entered selected parameter value to a predefined limit of the selected parameter, and increasing the stiffness of the input mechanism and changing the displayed value of the selected parameter if the entered selected parameter value is within the predefined limit.

A further embodiment includes locking the input mechanism from further movement if the entered selected parameter value is equal to the predefined limit.

Another further embodiment includes enabling the user to continue to move the input mechanism to change the entered selected parameter value.

Yet another further embodiment includes enabling the user to change the predefined limit of the selected parameter.

Other embodiments include providing an audible or visual warning to the user via the user interface when the entered selected parameter value is equal to the predefined limit.

A further aspect includes moving the user interface input mechanism in a second direction toward a target value of the selected parameter, computing the proximity of the entered selected parameter value to the target value of the selected parameter, and decreasing the stiffness of the input mechanism and changing the displayed value.

In one embodiment, the analyte is glucose, the apparatus comprises an insulin infusion pump, and the selected parameter is a bolus dose.

In another embodiment, movement of the user interface input mechanism in the first direction increases the value of the target bolus dose and the predefined limit is a maximum value of a bolus dose.

In one embodiment, the analyte is glucose, the apparatus comprises an insulin infusion pump, and the selected parameter is a basal rate.

In another embodiment, movement of the user interface input mechanism in the first direction increases the value of the target basal rate and the predefined limit is a maximum value of a basal rate.

While the present disclosure has been described with reference to the specific embodiments thereof, it should be understood by those skilled in the art that various changes may be made, and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

The invention claimed is:

1. A continuous glucose monitoring system, comprising:
    (1) a skin-mounted sensor control unit, comprising:
        a transcutaneous glucose sensor, a portion of which is configured for transcutaneous positioning in a subcutaneous tissue of a user, and wherein the transcutaneous glucose sensor is configured to sense one or more glucose levels in a body of the user;
        an adhesive patch disposed on a bottom surface of the skin-mounted sensor control unit, the adhesive patch configured to adhere the skin-mounted sensor control unit to skin of the user; and
        a wireless communication module configured to wirelessly communicate data indicative of the one or more glucose levels to a glucose monitoring device according to a Bluetooth communication protocol; and
    (2) the glucose monitoring device, comprising:
        a processor;
        a transceiver configured for wireless communication with the skin-mounted sensor control unit; and
        a user interface controllable by the processor, the user interface comprising a touch screen display configured for tactile contact by the user, wherein the touch screen display is configured to visually display a graph of the user's one or more glucose levels,
wherein the graph comprises a first axis corresponding to time and a second axis corresponding to the one or more glucose levels, and
wherein the touch screen display is further configured to provide a haptic feedback response in response to incrementing or decrementing, by the user, a selected glucose level of the one or more glucose levels along the first axis corresponding to time.

2. The continuous glucose monitoring system of claim 1, wherein the haptic feedback response comprises a discrete sensation.

3. The continuous glucose monitoring system of claim 1, wherein the touch screen display is further configured to visually output a numeric value associated with each selected glucose level of the one or more glucose levels in response to each incrementing or each decrementing by the user.

4. The continuous glucose monitoring system of claim 1, wherein the touch screen is further configured to provide a plurality of haptic feedback responses in response to inputted movement, by the user, in one or more directions associated with the incrementing or the decrementing of the selected glucose level of the one or more glucose levels along the first axis corresponding to time.

5. The continuous glucose monitoring system of claim 4, wherein the plurality of haptic feedback responses comprises a plurality of discrete sensations of equivalent magnitude.

6. The continuous glucose monitoring system of claim 5, wherein each discrete sensation of the plurality of discrete sensations is associated with a corresponding increment in the value or a corresponding decrement of the selected glucose level of the one or more glucose levels along the first axis corresponding to time.

7. The continuous glucose monitoring system of 4, wherein the one or more directions includes a first direction, wherein inputted movement in the first direction is associated with increasing a time value along the first axis corresponding to time.

8. The continuous glucose monitoring system of 7, wherein the one or more directions includes a second direction, wherein inputted movement in the second direction is associated with decreasing the time value along the first axis corresponding to time.

9. The continuous glucose monitoring system of claim 1, wherein the touch screen display is further configured to visually display an angular icon associated with a rate of change of the one or more glucose levels.

10. The continuous glucose monitoring system of claim 1, wherein the touch screen display is further configure to visually display a numeric value associated with a real time glucose level of the user.

11. The continuous glucose monitoring system of claim 1, wherein the glucose monitoring device is configured to output a vibratory alert associated with a reminder to replace the transcutaneous glucose sensor after ten (10) days.

12. The continuous glucose monitoring system of claim 1, wherein the glucose monitoring device is configured to output a vibratory alert associated with a reminder to replace the transcutaneous glucose sensor after fourteen (14) days.

13. The continuous glucose monitoring system of claim 1, wherein the glucose monitoring device is configured to output a vibratory alert associated with a reminder to replace the transcutaneous glucose sensor after an end of a useful life of the transcutaneous glucose sensor.

14. The continuous glucose monitoring system of claim 1, wherein the glucose monitoring device is configured to output a vibratory alert when a trend of the one or more glucose levels is indicative of potential hypoglycemia.

15. The continuous glucose monitoring system of claim 1, wherein the glucose monitoring device comprises an electromagnetic motor configured to generate the haptic feedback response.

16. The continuous glucose monitoring system of claim 15, wherein the electromagnetic motor comprises a voice coil.

17. The continuous glucose monitoring system of claim 1, wherein the glucose monitoring device comprises radio frequency identification (RFID) components.

18. The continuous glucose monitoring system of claim 1, further comprising:
(3) a medication delivery device, and
wherein the transceiver of the glucose monitoring device is further configured for wireless communication with the medication delivery device.

19. The continuous glucose monitoring system of claim 18, wherein the medication delivery device is an insulin infusion device.

* * * * *